(12) United States Patent
Daffer et al.

(10) Patent No.: US 6,497,717 B1
(45) Date of Patent: Dec. 24, 2002

(54) THERAPY STEAM AND HEAT TREATMENT CABINET

(75) Inventors: Steven J. Daffer, Edina, MN (US); Richard W. Jostrom, Mound, MN (US)

(73) Assignee: Visibelle Derma Institute, Inc., Bloomington, MN (US)

( * ) Notice: Subject to any disclaimer, the term of this patent is extended or adjusted under 35 U.S.C. 154(b) by 0 days.

(21) Appl. No.: 09/690,317

(22) Filed: Oct. 17, 2000

Related U.S. Application Data

(63) Continuation-in-part of application No. 09/289,628, filed on Apr. 12, 1999, now abandoned.

(51) Int. Cl.7 .............................................. A61H 21/00
(52) U.S. Cl. ........................................... 607/83; 607/81
(58) Field of Search ............................. 607/81–84, 87, 607/91; D24/203, 202; 4/524, 529

(56) References Cited

U.S. PATENT DOCUMENTS

| 1,221,163 A | 4/1917 | Frink |
|---|---|---|
| 1,797,916 A | 3/1931 | Kruse |
| 2,012,221 A | 8/1935 | Clark et al. |
| 2,096,128 A | 10/1937 | Mortrude, Jr. |
| 2,240,819 A | 5/1941 | Waly |
| D189,951 S | 3/1961 | Cosper |
| 3,409,915 A | 11/1968 | Jauvais |
| 3,772,713 A | 11/1973 | Roullier |
| 3,945,058 A | 3/1976 | Gardner |
| 4,031,573 A | 6/1977 | Romanoff |
| D249,894 S | 10/1978 | Brancaccio et al. |
| 4,130,120 A | 12/1978 | Kohler, Jr. |
| D255,491 S | 6/1980 | Brancaccio et al. |
| 4,258,706 A | 3/1981 | Shank |
| 4,277,855 A | 7/1981 | Poss |
| 4,565,188 A | 1/1986 | Hardie |
| 4,671,284 A | 6/1987 | Wilson et al. |
| 4,712,538 A | 12/1987 | Hardie et al. |
| 4,833,739 A | 5/1989 | Sakakibara et al. |
| 4,862,526 A | 9/1989 | Berger |
| 4,884,574 A | 12/1989 | Hardie et al. |
| 5,101,809 A | 4/1992 | Daffer et al. |
| 5,228,150 A | 7/1993 | Parker ........................... 4/568 |
| 5,255,399 A | 10/1993 | Park |
| 5,416,931 A | 5/1995 | Wolfenden et al. |
| D360,469 S | 7/1995 | Panelli et al. |
| 5,441,529 A | 8/1995 | Dorsch |
| 5,511,254 A | 4/1996 | O'Brien |
| 5,546,678 A | 8/1996 | Dhaemers |
| 5,645,578 A | 7/1997 | Daffer et al. |
| 6,004,344 A | 12/1999 | Fujii |

FOREIGN PATENT DOCUMENTS

| DE | 725804 | 3/1944 |
|---|---|---|
| FR | 2086905 | 12/1971 |
| FR | 2629343 | 10/1989 |
| GB | 1490381 | 11/1977 |
| JP | 8112302 | 5/1996 |

Primary Examiner—Justine R. Yu
(74) Attorney, Agent, or Firm—Westman, Champlin & Kelly, P.A.

(57) ABSTRACT

A personal treatment device comprising a personalized capsule that has a bed for a person to lie thereon in a supine position, the capsule has a cover that is openable for access to the bed and closeable to define a chamber in which a person lies. The cover has a divider adjacent a head portion of the bed, such that the head of a user will extend out of the cover. Suitable heaters are provided in the cover to radiate energy onto a person on the bed, and a steam generator is provided for adding steam as desired to the interior of the chamber and also to direct steam toward the face of a user under control of the user.

18 Claims, 8 Drawing Sheets

THERAPY STEAM AND HEAT TREATMENT CABINET

CROSS-REFERENCE TO RELATED APPLICATION

This application is a continuation-in-part of U.S. application Ser. No. 09/289,628, filed Apr. 12, 1999, entitled THERAPY STEAM AND HEAT TREATMENT, now abandoned.

BACKGROUND OF THE INVENTION

The present invention relates to a personalized therapy cabinet or enclosure having a bed on which a person will lie and be treated with both heat and steam therapy on an individually controlled basis to permit a person to provide overall therapy.

Individual personalized saunas have been advanced, as shown in U.S. Pat. No. 5,101,809, and these devices have used dry heat for providing a pleasant environment for a person reclining on a vibratable bed. Steam has also been used in cabinets such as U.S. Pat. No. 3,409,915, which shows a vibrating, reclining chair with a hood on the outside that carries a speaker, a fan and an oxygen inlet. The steam supply also is provided to the interior of this type of cabinet. Various other steam sauna or steam cabinets have been advanced as well.

U.S. Pat. No. 5,645,578, shows a compartment having treatment with light and heat, together with a vibratable bed.

SUMMARY OF THE INVENTION

The present invention relates to a personalized cabinet which includes a bed, and which has an array of interior heaters for providing controllable dry heat to a user, and which further has one or more steam sources controlled for providing steam to the interior of the cabinet. Steam is provided on the interior of the cabinet and ducts can be used for directing the steam to various locations for desired therapeutic treatment. There are also steam outlets on a control panel that direct steam onto the face of a riser. A removable transparent tunnel hood can be placed over the head of the user to direct the steam over the face.

A fan is used to provide a positive pressure to insure proper steam distribution.

By providing a combination of heat and steam with a full length bed, which can be vibrated if desired, the treatment can take place as needed for complete relaxation and therapeutic applications of both radiating heat and steam.

DETAILED DESCRIPTION OF THE PREFERRED EMBODIMENTS

Figure 1:
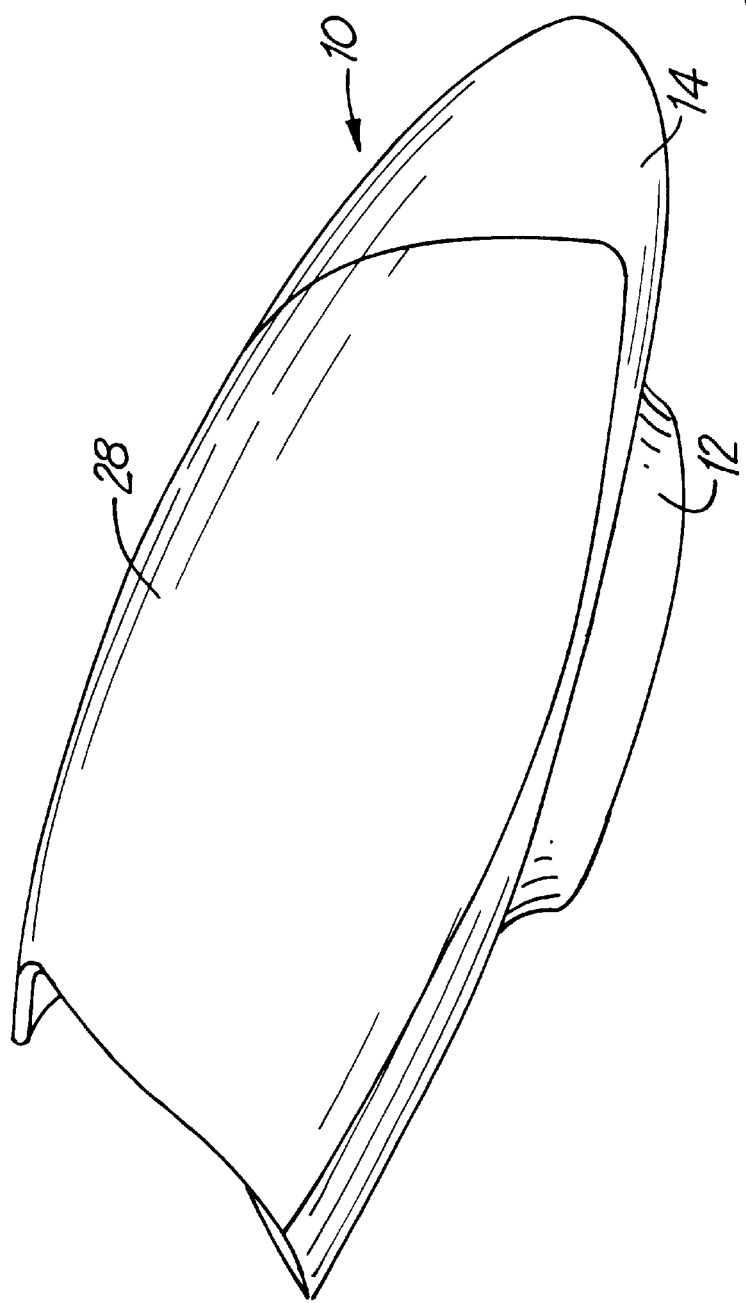
FIG. 1 is a perspective view of a personal therapy compartment made according to the present invention shown in a closed position.

A personalized compartment illustrated generally at 10 comprises a base 12 that rests on the floor or surface, and supports a hollow cabinet type structure 14 that defines an interior chamber or compartment 16. A bed support wall 17 is supported on the interior and configured to form a bed 18. The bed 18 is provided with a plurality of cushions, as shown individual cushions 20A, 20B and 20C for supporting the legs, and torso. A pillow 22 is also provided for resting a user's head (shown in dotted lines in FIG. 2 at 26) on an exterior of the cabinet when the cover indicated at 28 is closed.

The base 12 is made with a bottom wall 13 which, with the bed support wall 17, forms an interior chamber shown at 32 (FIG. 5), in which a steam generating 34 is mounted. The steam generating includes a heater assembly 35, shown schematically in FIG. 4 that is in a water tank 36, and when powered, generates steam which is provided through a pair of exhaust outlets indicated at 40 and 41. The exhaust outlet 40 is connected to a duct 43 that extends to an outlet port opening 40A on a side flange 45 of the bed support wall 17.

The outlet 41 connects to a duct 42 which leads to a port or opening 41A on a side flange 47 of the bed support wall 17.

Figure 5:
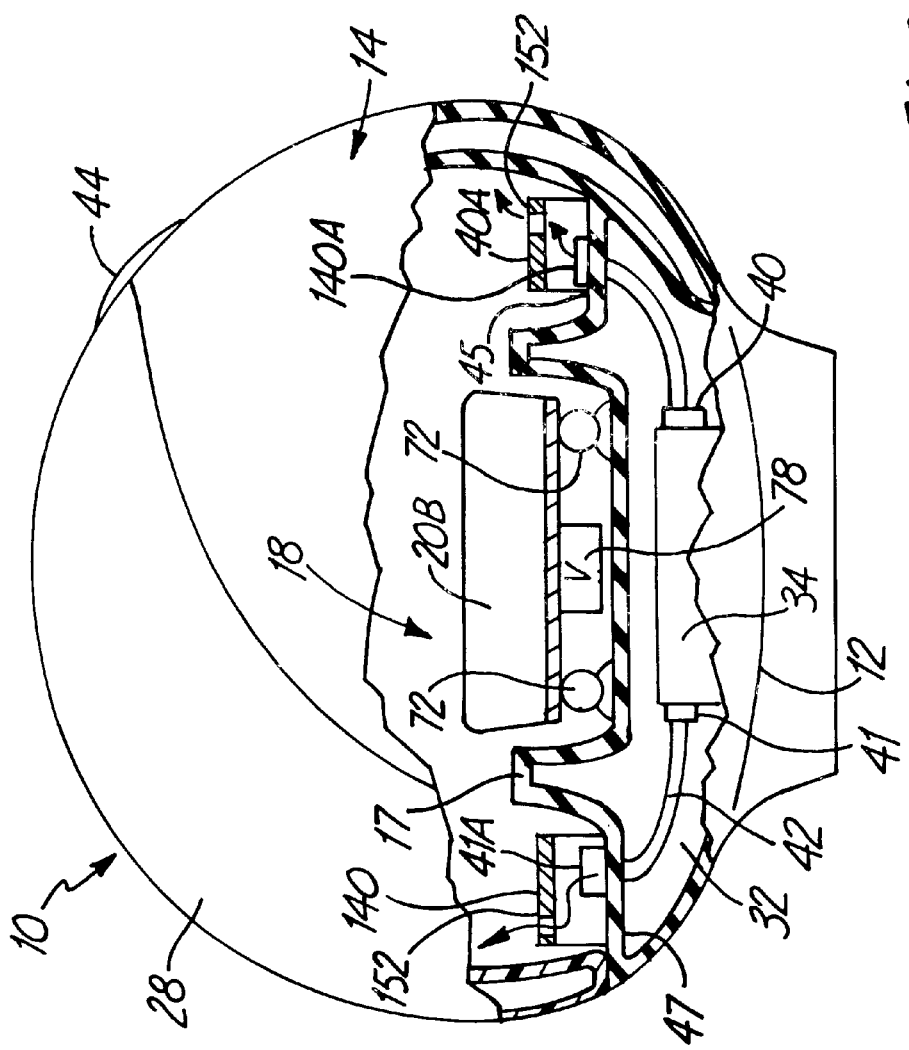
FIG. 5 is a partial sectional view taken on line 5—5 in FIG. 4

It can be seen that the base 12 and the cover 28 can be molded with a double wall construction as shown schematically in FIG. 5. The double wall can form steam passageways or ducts to provide steam spouts below the bed wall 17 or in the cover 28 to discharge steam into the interior chamber 16 formed by base 12 and cover 28. The outlet opens for steam can be at desired locations, but the outlets or spouts shown at 40A and 41A are along the sides, on the flanges, to direct steam into the interior chamber 16 where a use will be resting on the bed 18.

The cover 28 is hinged with suitable hinges 44 to the base 12. The base 12 extends upwardly on one side a substantial distance, and the cover is arranged so that it can be raised and lowered from an open position shown in FIG. 4, to a closed position shown in FIGS. 1, 2, 3 and 5.

Figure 4:
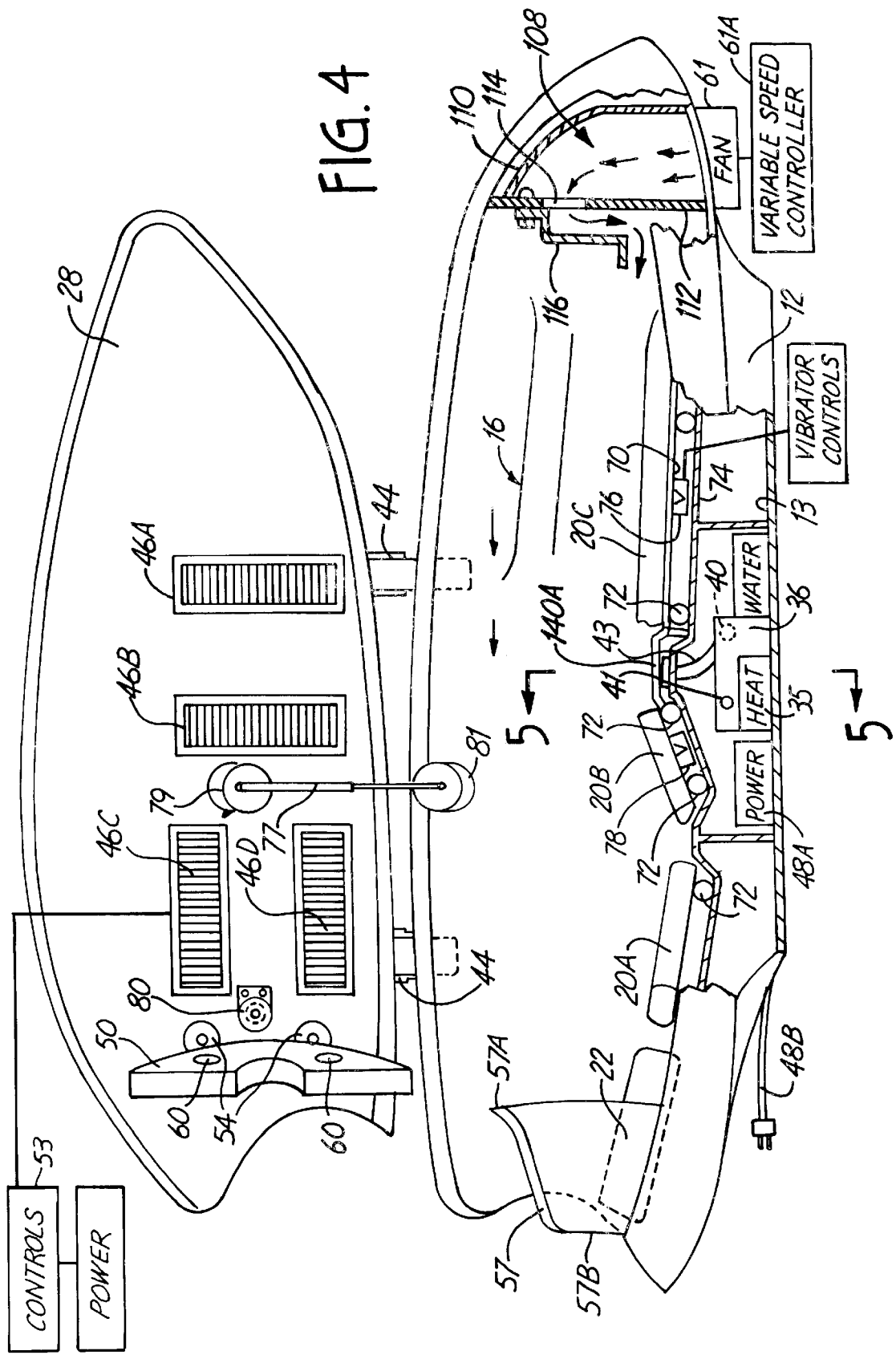
FIG. 4 is a side view of the compartment of FIG. 1 shown in the cover with an open position.

The cover is provided with a plurality of infrared heaters indicated generally at 46A, 46B, 46C and 46D in FIG. 4. These heaters are constructed so that they will operate safely, and powered from a power source indicated schematically at 48, through controls 53 shown schematically. The controls 53 are on a divider panel 50, that has a neck opening 52 and which is attached to the cover at the head end as shown at 54.

Figure 3:
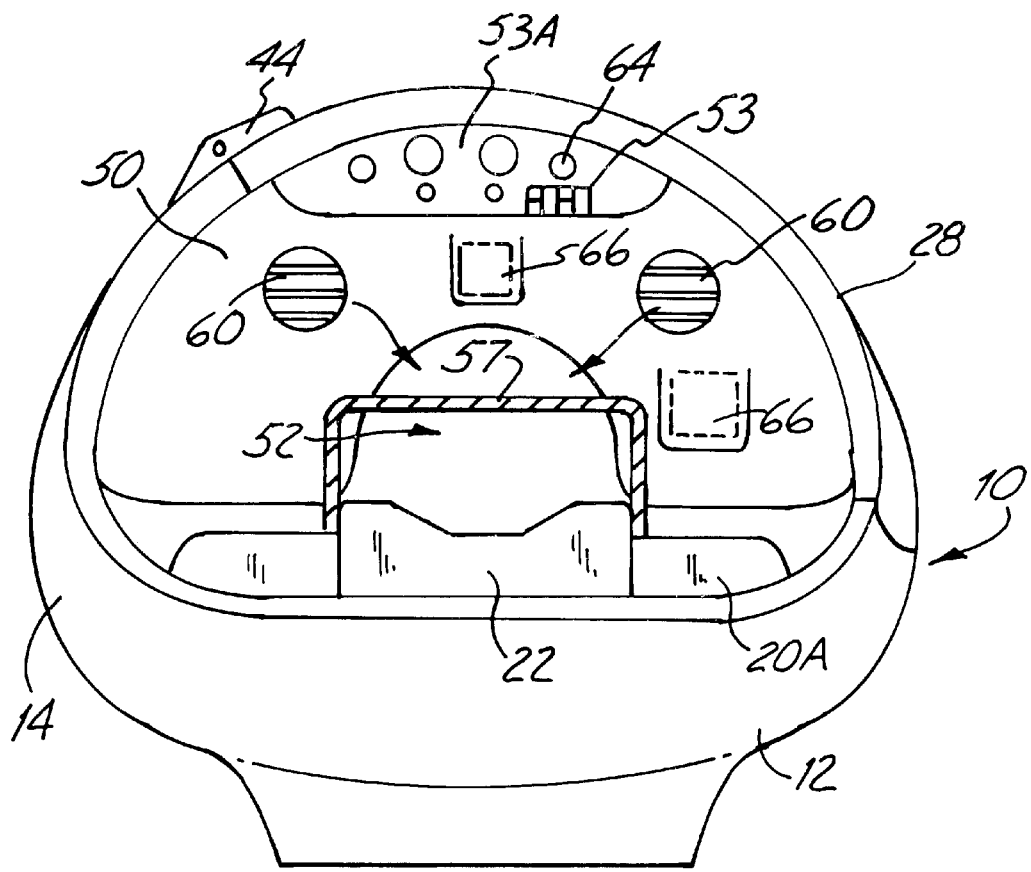
FIG. 3 is an end view thereof illustrating the control panel and selected steam outlets.

The divider panel 50 is provided with the controls 53 on a control panel 53 as shown in FIG. 3. The control panel is near an upper side of the divider 50. The controls 53 include on-off switches for each heater, and a thermostat 64 to control the maximum, and if desired, the minimum temperatures in compartment or chamber 16. The thermostat can be responsive to temperature sensors in the chamber 16.

The divider panel 50 has steam outlet openings 60 at desired locations to permit steam to exhaust onto the face of a user. The steam outlets 60 are of the type that are louvered and controllable, so that they can be shut off, or rotated to direct the exhausted steam in selected directions, similar to the outlets of air conditioning and heating ducts in an automobile. These are conventional louvers that are shown at the outlet openings 60.

Figure 6:
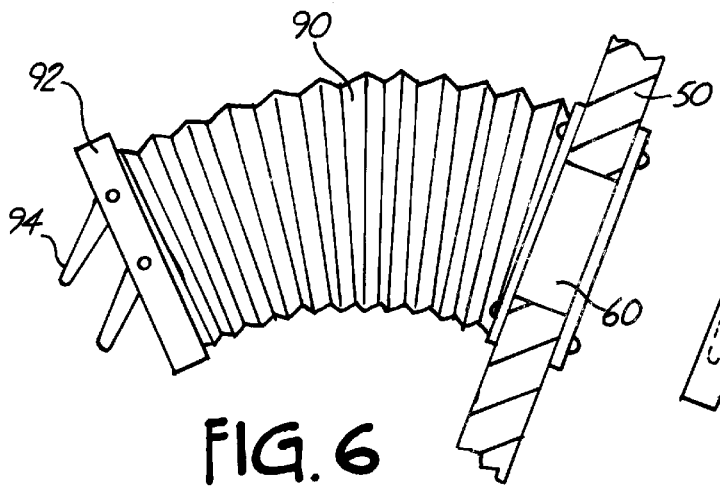
FIG. 6 is a fragmentary view of the control panel showing a modified steam outlet comprising a flexible tube that can be directed to portions of the user's face and head.
Figure 7:
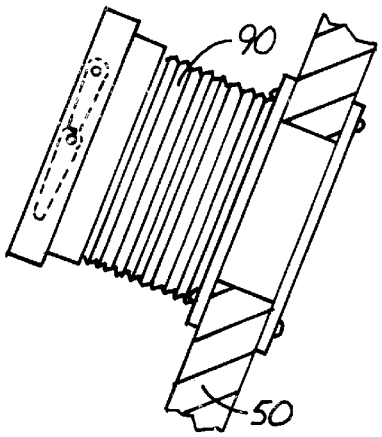
FIG. 7 is a view of the device of FIG. 6 in a stored or collapsed position.

As shown in FIGS. 6 and 7, the outlet openings 60, instead of having louvers over the openings can be connected to flexible tubes 90 (one of which is shown) over each of the outlet openings 60, or to only one outlet opening. The flexible tube 90 will have a support ring 92 at its outer end with pivoting louvers 94 that can be adjusted in a normal manner.

As shown in FIG. 7, this flexible tube 90 can be collapsed or compressed, so that it does not protrude far beyond the panel 50, as shown. The tubes permit the user to extend the outlet for steam and move it around. The tubes 90 can be used to direct steam in desired locations, to give greater versatility to the treatment.

Alternatively, a transparent duct or housing 57 can be provided to direct steam over the user's face when desired. The duct is open ended and intercepts the steam flow from outlets 60 at the inner end 57A, and steam then flows across the user's face and out the outer end 57B. The duct or housing size can be selected as desired. The inner end can be tilted up or have scoops to catch the steam from outlets 60. The flexible tubes 90 would not be used when the duct 57 is used.

Figure 8:
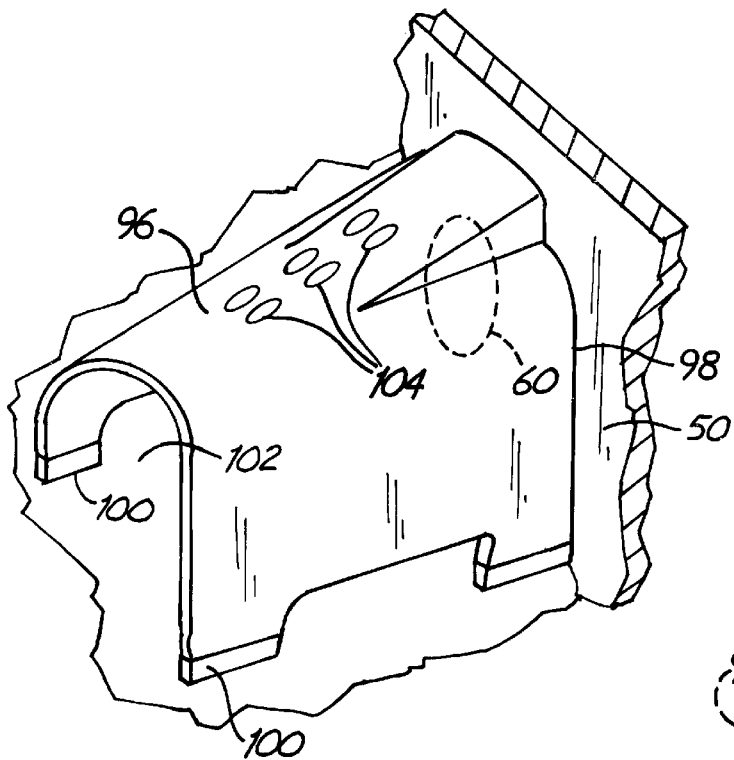
FIG. 8 is a perspective view of a modified steam hood used with the present invention.

A first modified form of the facial steam housing or duct is shown in perspective view in FIG. 8. There, the duct 96 is molded, and has an end 98 that fits against the panel 50, if desired, and the outlet 60 would be inside the duct as shown in dotted lines in FIG. 8. This duct is molded into more of a streamlined shape, and includes support pads 100, that will rest on support walls of the housing in a suitable position. An opening 102 is provided, but the head of a person can actually fit within this duct, and sight openings 104 are provided in the top wall so that a person inside the duct is able to read the gauges and other instruments on the panel. This duct 96 is removable, if desired as well.

Figure 8A:
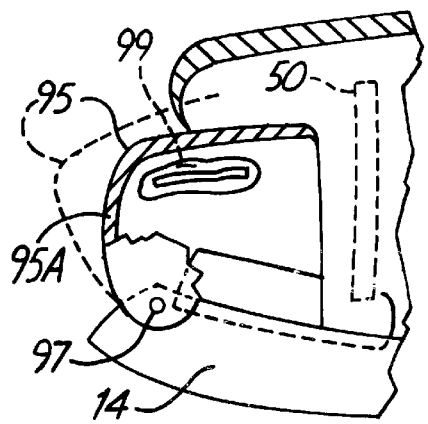
FIG. 8A is a further modified form of a steam hood used with the present invention.

A second modified form of a facial steam duct or hood is shown in FIG. 8A. A housing or hood 95 that can be transparent or opaque has a wall that encloses the head of a user and tapers around the end of the compartment with a wall section 95A to enclose the head of a user. The hood 95 can be hinged as at 97 so it will open as shown in dotted lines. If desired the closed end hood 95 can have side edges shaped as in the form shown in FIG. 8 and supported on the interior of the head end of the compartment, instead of being hinged. This hood is similar to the hood shown in U.S. Pat. No. 5,645,578, and can include lights shown schematically at 99 that is intense enough light therapy, as described in that patent.

The thermostat 64 also can be connected to the heater 35 of the steam generator to control the steam generator for turning it on and turning it off when the temperature is outside desired limits. A separate thermostat can be used for controlling the heaters 46A–46D. Each of the heaters 46A–46D can be individually controlled by thermostat, if desired, or one temperature setting can control all of the heaters simultaneously.

The interior chamber 16 will be held above atmosphere pressure as steam generates so a flow out of openings or ports 60 will occur. A fan 61 is mounted at the foot end and can be turned on to create greater pressure, particularly when steam is to be discharged from outlets 60. The fan 61 is variable speed and controlled with a controller 61A. The flow indicated by arrows 61B creates movement of the steam across the body and out the ducts so they are opened, for satisfactory therapy.

Figure 2:
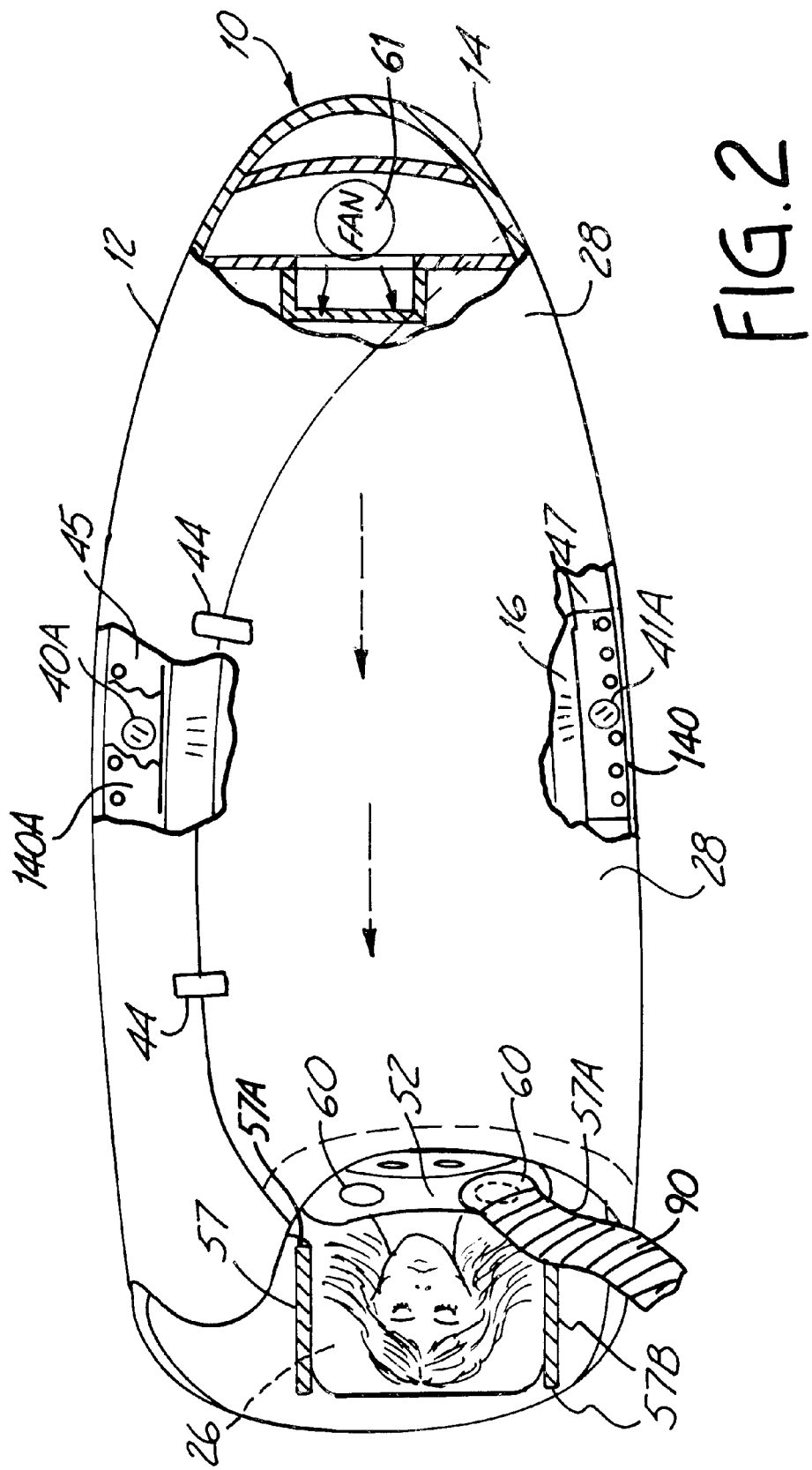
FIG. 2 is a top plan view of the compartment of FIG. 1 illustrating schematically the positioning of a person in the compartment of FIG. 1.

As shown in FIGS. 2 and 4, the fan 61 can discharge into a ducting system indicated generally at 108, and the interior of the housing can have a duct wall 110 formed therein, so that the fan discharges upwardly against this wall. A divider wall 112 can complete the duct, and an opening 114 leads into the chamber 16 where a person rests. A deflector wall 116 can be provided (it can be removable) so that the airflow goes downwardly at the foot end, and does not discharge directly into the upper portions of the chamber. This ducting, including the deflector 116 for deflecting flow downwardly, insures that steam generated and which is subjected to an increased pressure by fan 61 so that it will discharge out through the opening 60, will not exhaust directly across a user but will be deflected down for flow control. The fan pressure causes steam to discharge through opening 60 and one of the facial ducts used or through the flexible tubes 90 as desired. Adequate pressure will be provided for such use.

A simple hand opening 66 covered with a flap will permit a person to reach the controls with the arm inside the chamber 16.

Figure 9:
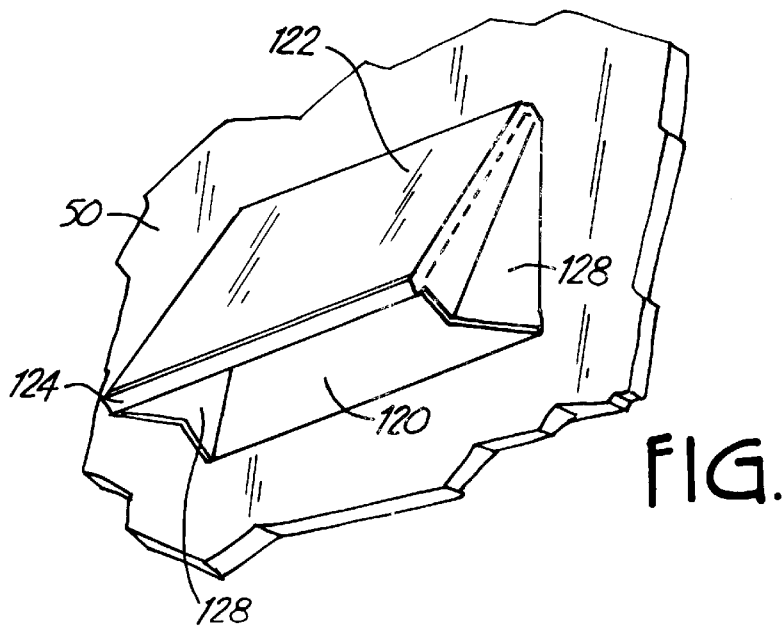
FIG. 9 is a fragmentary view of the panel at the head end of the housing with a further modified form of a combined steam outlet and access opening cover.
Figure 10:
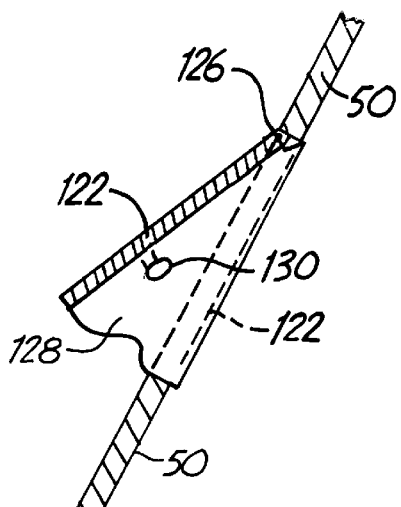
FIG. 10 is a side sectional view of the device of FIG. 9 in a position to direct steam toward the face of a user.
Figure 11:
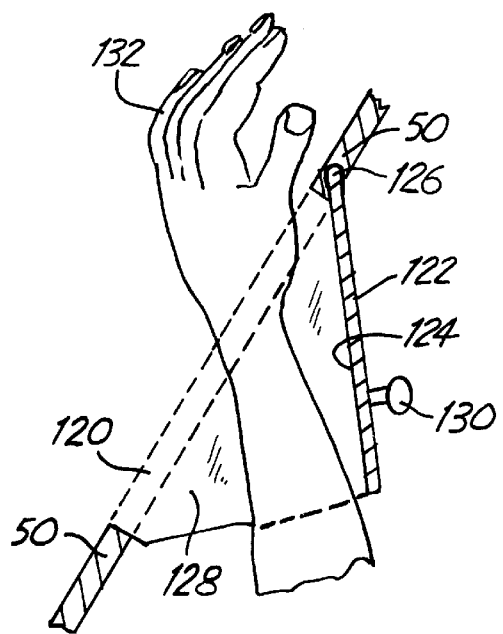
FIG. 11 is a view shown with the cover moved inside the housing so that a hand illustrated schematically can extend through the opening for access to the controls of the unit.

FIGS. 9, 10 and 11 show a modified steam outlet configuration, and hand and arm access opening. As shown in FIG. 9, the panel 50 which is shown fragmentarily can have an opening 120 therethrough, and a door panel 122 that can be formed of a fabric, and reinforced with a plastic plate indicated at 124, the fabric can be secured in a suitable manner to the panel 50 at the upper edge of opening 120, as shown in FIG. 10. The fabric or other flexible material is made to form a hinge 126 (FIGS. 10 and 11). The panel 124 forms a cover for the opening 120, and the sides are connected with a folding or gusseted flexible material 128 on each of the sides, to provide a shield for steam to be ducted out as indicated by arrows toward the face of a user.

The dotted lines showing of 122 in FIG. 10 is with the panel 122 in closed position, and it can be held there with a suitable friction type connection, or a snap catch. A finger knob 130 can be utilized for moving the panel. The panel 122 can be pulled inwardly to the interior chamber 16, as shown in FIG. 11, to provide an access opening for a hand 132 to protrude through the opening 120 to operate control knobs or do other tasks on the outside of the panel 50. The hands of a person in the chamber 16 are inside the chamber and on the inside of the panel 50.

The panel 122 can be reinforced with the suitable material 124, or can be made as a separate panel with flexible side gussets 128 and a flexible hinge 126 separately formed. Adjustment of the panel controls the amount of steam coming out, and also then provides for exterior access for the hand of a person whose arms are inside the chamber 16.

As can be seen, the heaters 46A and 46B over the legs extend transversely to the longitudinal axis of a person or of the bed, and the heaters 46C and 46D, which are in the chest and torso area are extending longitudinally along the length of the person being heated, and are spaced apart a selected distance.

A suitable gas spring indicated at 77 can be provided for maintaining a cover in an open position, and has opposite members mounted at 79 and 81 to the cover and base cabinet, respectively.

A power box or power source indicated at 48A can be provided in the base, for the steam generator as shown schematically in FIG. 4. Suitable connection cords pass out through the wall of the cabinet and are connected to house current. Such power cords such as shown at 48B can be maintained at any desired position.

The individual cushions forming the bed, shown at 20A–20C are supported so that they can be vibrated for vibration at the same time that steam and heat are being felt by the body. Schematically illustrated for cushion 20C is a cushion support panel 70, that is supported on suitable elastomeric or resilient balls 72 relative to the bed wall 17 in a recessed portion shown at 74. A vibrator 76 can be mounted onto the panel 70, and controlled from the control panel 52 to provide vibration as desired. Additionally, the cushion 20B is in a position where it is supported on elastomeric ball 72 (it would be supported at all four corners) and a vibrator 78 can be used for vibrating the smaller cushion 20B. The same type of support on elastomeric balls 72 can be used for the cushion 20A as well, and thus, individual vibration sensations can be obtained by the user. The vibrations can be individually controlled manually or can be programmed to be energized at preselected times.

This type of vibration mounting is shown in U.S. Pat. No. 5,101,809.

Additionally, if desired, aroma therapy treatment can be added by adding outlets on the divider panel 52 and a source of aroma placed on the interior of the chamber that would be controlled by the operator. Music can be added as well for therapy of the user, but the addition of the steam in the interior compartment as well as the infrared heat permits satisfactory individually controlled therapy. Adding lights further to the interior of hood 95 as shown in U.S. Pat. No. 5,645,578 adds light therapy treatment.

The steam generator used is a commercially available unit, and can be selected in size to accommodate the size of the chamber 16 as desired. Additional steam outlet spouts or ports can be provided in either the cover 28 or in the base 12, at desired locations, and these outlets can be individually controlled with suitable valves or louvers.

Figure 12:
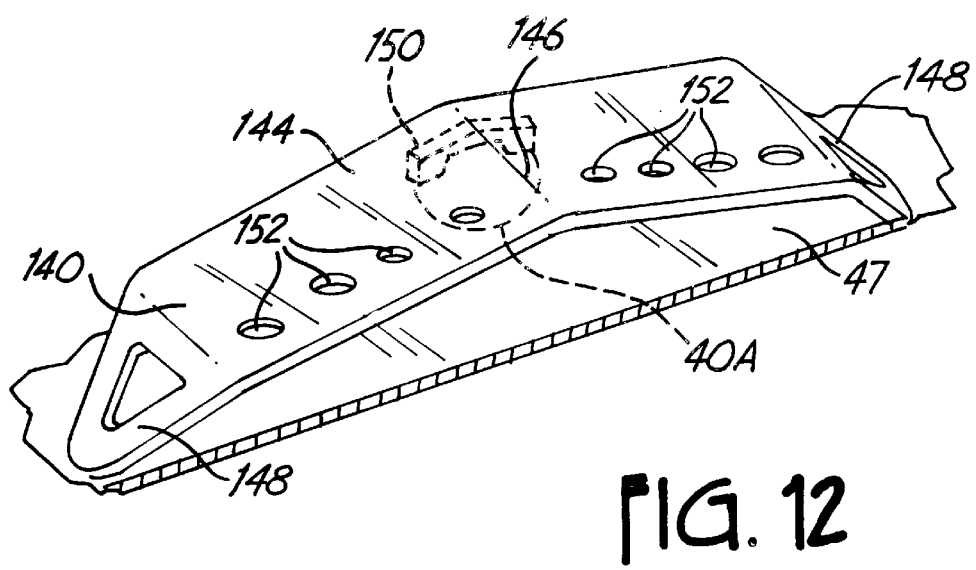
FIG. 12 is a perspective view of a steam deflector that is used over the steam outlets, if desired, with the device of the present invention, which also are shown in FIG. 2.

As shown in FIGS. 2 and 12, schematically, the steam outlets 40A and 41A can be covered with steam deflector assemblies 140 and 140A. The steam deflector assemblies can be made of a suitable plastic material and secured in place on the flanges 45 and 47 that carries the steam outlets. The steam ducts can have sufficient length to support the deflectors 140 and 140A, as desired. The deflector 140 is shown in FIG. 12, and it is a right-hand deflector but the left-hand deflector 140A is a mirror image of this. It can be a panel 144 of plastic that is formed in a desired shape, as shown, tapered upwardly toward a center line 146. End members 148 can be provided to be supported on portions of the housing, such as the flange 47, of the bed support wall. The deflector can be secured in place with suitable clips, or merely rested in position if it is desired to remove or move them from time to time. The center portions of the deflector panel 144 can have a support member 150 that is shown in dotted lines, that would overlie the steam duct 40A. The panel 144 has a series of steam discharge openings 152 along its length so that the steam is deflected to come out along the sides of the cover and the housing, and flow upwardly the sides as shown by arrows in FIG. 5. The steam deflectors 140 and 141 help distribute the steam as desired. The side flanges 45 and 47 can be formed to receive the end portions 148, if desired. The deflectors again divert the steam coming out of the main outlets to be diffused out through a plurality of openings that are adjacent to the side walls and cause the steam to flow upwardly along the side walls. The fan 61 also then will provide a flow of steam toward the panel 50, and out across the face of the user.

If desired, a small fan, such as that shown at 80 in FIG. 4, can be provided in addition to main fan 61 for moving additional steam through the openings or ports 60, and as stated, direct steam outlets could be provided as well through the double walled cover and small provided ducts connecting to the port 60 on the interior of the divider 50. The duct or tunnel 57 can be sized as desired.

Although the present invention has been described with reference to preferred embodiments, workers skilled in the art will recognize that changes may be made in form and detail without departing from the spirit and scope of the invention.

What is claimed is:

1. A personal treatment device having a support pedestal and an elongated generally horizontally extending bed supported by the pedestal, the bed being supported above a bottom wall of the pedestal and having a portion forming a head support, a cover member on said pedestal and openable to permit a person access to the bed and closable to enclose a chamber for a person on the bed, a divider panel adjacent a head end for enclosing the chamber and bed while excluding the head support such that a head of a person using the device is on an exterior of the chamber formed by the cover member and pedestal, a plurality of heaters mounted in the cover member on an interior thereof, and positioned to direct heat energy onto a person lying on the bed, and a steam generator mounted in the device between the bed and the bottom wall and having at least one steam duct extending along the bed on at least one side of the bed and having an upwardly facing outlet opening for discharging steam alongside the bed into the chamber in direction toward the cover member.

2. The personal treatment device of claim 1, wherein there are two steam ducts, one on each side of the bed and discharging steam on both sides of person lying on the bed.

3. The personal treatment device of claim 2, wherein said heaters comprise a pair of infrared heaters having generally rectangular shapes, the pair of infrared heaters being spaced laterally apart and extending transversely to a longitudinal direction above the bed adjacent an end of said bed opposite from the driver.

4. The personal treatment device of claim 6 and a second pair of heaters of rectangular configuration on the cover extending parallel to the longitudinal axis adjacent a midportion of the bed.

5. The personal treatment device of claim 4 and a bed wall supporting the bed, the bed wall having flanges on lateral sides thereof, and at least one steam duct being connected to an opening in one of the flanges.

6. The personal treatment device of claim 1, wherein said divider has an outlet opening therein, for providing steam on the exterior of the divider directed toward the face of a person lying on the bed.

7. The personal treatment device of claim 6, further comprising a flexible hose connected to the outlet opening, and having a discharge end on the exterior of the divider, the discharge end being movable by a person lying on the bed with a head on the exterior of the divider.

8. The personal treatment device of claim 6 and a housing to overly the head of a user, the housing having an open end to receive steam from the outlet opening.

9. The personal treatment device of claim 8 wherein the housing has a closed end portion opposite the open end.

10. The personal treatment device of claim 9 and a light for light therapy on the interior of the housing.

11. The personal treatment device of claim 1 further comprising a deflector for steam over the outlet opening of the steam duct for deflecting the steam in a desired location, said deflector comprising a panel having a length and overlying the steam outlet opening, and the deflector having openings spaced along the length thereof.

12. The personal treatment device of claim 1, wherein said steam duct is adjacent a side of the bed and is substantially level with said bed.

13. The personal treatment device of claim 1, and an auxiliary fan at an end of the chamber opposite from the head end, said fan being energizable to direct air toward the head end to carry steam in the chamber with airflow formed by the fan.

14. The personal treatment device of claim 13, and a baffle wall for directing airflow from said fan downwardly as it enters the chamber.

15. A method of providing therapy to a person in a personalized chamber including providing a bed on which a person can lie, enclosing a person in a chamber with a head of the person extending out of the chamber on a head support, providing controllable radiant heaters in the chamber above the bed, providing steam on the interior of the chamber for treatment purposes, directing steam through outlet openings from the chamber toward the head support, and providing a flexible hose on at least one outlet opening, and manually adjusting the flexible hose to direct steam in a desired location on the head support.

16. The method of claim 15 including providing outlet openings adjacent the head of a person on the bed for permitting steam to exhaust toward the head.

17. The method of claim 16, including providing flexible hoses on the outlet openings, and manually adjusting the flexible hoses to direct steam in a desired location.

18. A personal treatment device having a support base having a recessed interior, a bed support wall on the recessed interior having generally horizontal flanges joined to the base on sides of the base, an elongated generally horizontally extending bed supported on the bed support wall between the flanges, above a bottom wall of the base and having a portion forming a head support, a cover member on said base and openable to permit a person access to the bed, and closable to enclose a chamber for a person on the bed, a divider panel adjacent a head end for closing one end of the chamber while excluding the head support such that a head of a person on the bed is on an exterior of the chamber formed by the cover member, a heater to heat the chamber, a steam generator mounted between the bed support wall and the bottom wall, a pair of steam ducts extending along the bed to the flanges on the sides of the bed and each having an upwardly facing outlet opening for discharging steam alongside the bed into a chamber, and a deflector panel on each flange, spaced above the flange and overlying the respectively outlet opening, the deflector panels each having a plurality of openings spaced along the panel for directing steam from the duct respective outlet into the chamber.

* * * * *

UNITED STATES PATENT AND TRADEMARK OFFICE
CERTIFICATE OF CORRECTION

PATENT NO. : 6,497,717 B1
DATED : December 24, 2002
INVENTOR(S) : Steven J. Daffer and Richard W. Jostrom It is certified that error appears in the above-identified patent and that said Letters Patent is hereby corrected as shown below:

Column 6,
Line 54, cancel "6" and insert -- 3 --.

Signed and Sealed this

Twenty-first Day of September, 2004

JON W. DUDAS
*Director of the United States Patent and Trademark Office*